(12) United States Patent
Leung et al.

(10) Patent No.: US 6,329,343 B1
(45) Date of Patent: Dec. 11, 2001

(54) BIOADHESIVE ANTIBACTERIAL WOUND HEALING COMPOSITION

(75) Inventors: Sau-Spence Leung, Parsippany; Alain Martin, Ringoes; Robert S. Leone, Fanwood, all of NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/511,869

(22) Filed: Feb. 25, 2000

Related U.S. Application Data

(60) Provisional application No. 60/121,784, filed on Feb. 26, 1999.

(51) Int. Cl.[7] .................................................. A01N 43/04
(52) U.S. Cl. ........................... 514/23; 514/458; 514/886; 514/887; 514/904
(58) Field of Search .............................. 514/23, 458, 904, 514/887, 886

(56) References Cited

U.S. PATENT DOCUMENTS

| | | | |
|---|---|---|---|
| 4,245,689 | 1/1981 | Grard et al. | 162/134 |
| 4,562,020 | 12/1985 | Hijiya et al. | 264/39 |
| 4,844,898 | 7/1989 | Komori et al. | 424/150 |
| 5,618,799 | 4/1997 | Inagi et al. | 514/53 |
| 5,658,956 | * 8/1997 | Martin et al. | 514/724 |
| 5,722,942 | 3/1998 | Tanaka et al. | 602/56 |

FOREIGN PATENT DOCUMENTS

| | | |
|---|---|---|
| 0258761 | 3/1988 | (EP) . |
| 0745392 | 4/1996 | (EP) . |
| 05065222 | 3/1993 | (JP) . |
| 63220876 | 9/1998 | (JP) . |
| WO9527501 | 10/1995 | (WO) . |
| WO9600584 | 1/1996 | (WO) . |
| WO9603149 | 2/1996 | (WO) . |
| WO9606640 | 3/1996 | (WO) . |
| WO9637228 | 11/1996 | (WO) . |

* cited by examiner

*Primary Examiner*—Kevin E. Weddington
(74) *Attorney, Agent, or Firm*—Barry H. Jacobsen

(57) ABSTRACT

A bioadhesive wound-healing composition includes pullulan, pyruvate, an antioxidant, and a mixture of saturated and unsaturated fatty acids. The composition can be provided in the form of a film that does not self-adhere. The composition can include additional medicinal agents, such as polymyxin B sulfate, bacitracin zinc, and neomycin sulfate. Methods for producing the composition and methods for treating wounds with the composition are also disclosed.

25 Claims, No Drawings

BIOADHESIVE ANTIBACTERIAL WOUND HEALING COMPOSITION

This application claims benefit of 60/121,784, filed Feb. 26, 1999.

FIELD OF THE INVENTION

This invention pertains to therapeutic bioadhesive wound-healing compositions useful for treating wounds. More particularly, the bioadhesive wound-healing compositions comprise pullulan and wound-healing agents and/or metabolites thereof. This invention also pertains to methods for preparing and using the bioadhesive wound-healing compositions and the pharmaceutical products in which the therapeutic compositions may be used.

BACKGROUND OF THE INVENTION

Wounds are internal or external bodily injuries or lesions caused by physical means, such as mechanical, chemical, viral, bacterial, or thermal means, which disrupt the normal continuity of structures. Such bodily injuries include, e.g., contusions, wounds in which the skin is unbroken, incisions, wounds in which the skin is broken by a cutting instrument, and lacerations, wounds in which the skin is broken by a dull or blunt instrument.

A wide variety of products have been developed that enhance the body's ability to heal itself when wounded. These products typically function by medicating the wound, isolating the wound from infectious agents, and/or by binding the wound to prevent wound growth and to minimize the gap that the body's natural repair mechanisms must bridge to heal the wound.

For example, U.S. Pat. No. 5,856,364 to Martin discloses a therapeutic antiviral wound-healing composition comprising an antiviral agent and a wound-healing composition comprising effective amounts of pyruvate; an antioxidant, preferably Vitamin E acetate; and a mixture of saturated and unsaturated fatty acids.

U.S. Pat. No. 5,692,302 to Martin et al. discloses a razor cartridge comprising a wound-healing composition delivery system fixed to the cartridge. The wound-healing composition comprises effective amounts of pyruvate; an antioxidant, preferably Vitamin B acetate; and a mixture of saturated and unsaturated fatty acids.

U.S. Pat. No. 5,674,912 to Martin discloses a sunscreen wound-healing composition comprising a sunscreen agent, an anti-inflammatory agent and a wound-healing composition comprising effective amounts of pyruvate; an antioxidant, preferably Vitamin B acetate; and a mixture of saturated and unsaturated fatty acids.

U.S. Pat. No. 5,663,208 to Martin discloses an anti-fungal wound-healing composition comprising an anti-fungal agent and a wound-healing composition effective amounts of pyruvate; an antioxidant, preferably Vitamin B acetate; and a mixture of saturated and unsaturated fatty acids.

U.S. Pat. No. 5,658,957 to Martin discloses an immunostimulating wound-healing composition comprising an immunostimulating agent and a wound-healing composition comprising effective amounts of pyruvate; an antioxidant, preferably Vitamin E acetate; and a mixture of saturated and unsaturated fatty acids.

U.S. Pat. No. 5,658,956 to Leung and Martin discloses a bioadhesive wound-healing composition comprising a bioadhesive agent and a wound-healing composition comprising effective amounts of pyruvate; an antioxidant, preferably Vitamin B acetate; and a mixture of saturated and unsaturated fatty acids.

U.S. Pat. No. 5,652,274 to Martin discloses a therapeutic wound-healing composition comprising effective amounts of pyruvate; an antioxidant, preferably Vitamin E acetate; and a mixture of saturated and unsaturated fatty acids.

U.S. Pat. No. 5,648,380 to Martin discloses an anti-inflammatory wound-healing composition comprising an anti-inflammatory agent and a wound-healing composition comprising effective amounts of pyruvate; an antioxidant, preferably Vitamin E acetate; and a mixture of saturated and unsaturated fatty acids.

U.S. Pat. No. 5,646,190 to Martin discloses an acne treating wound-healing composition useful for the topical treatment of acne vulgaris tretinoin and a wound-healing composition comprising effective amounts of pyruvate; an antioxidant, preferably Vitamin E acetate; and a mixture of saturated and unsaturated fatty acids.

U.S. Pat. No. 5,641,814 to Martin discloses an antikeratolytic wound-healing composition comprising an antikeratolytic agent and a wound-healing composition comprising effective amounts of pyruvate; an antioxidant, preferably Vitamin B acetate; and a mixture of saturated and unsaturated fatty acids.

U.S. Pat. No. 5,633,285 to Martin discloses a cytoprotective wound-healing composition comprising a cytotoxic agent and a wound-healing composition comprising effective amounts of pyruvate; an antioxidant, preferably Vitamin B acetate; and a mixture of saturated and unsaturated fatty acids.

U.S. Pat. No. 5,614,561 to Martin discloses an antihistamine wound-healing composition comprising an antihistamine and a wound-healing composition comprising effective amounts of pyruvate; an antioxidant, preferably Vitamin E acetate; and a mixture of saturated and unsaturated fatty acids.

U.S. Pat. No. 5,602,183 to Martin et al. discloses a dermatological wound-healing composition useful to minimize and treat diaper comprising a therapeutically effective amount of a buffering agent to maintain the pH of the composition and a wound-healing composition comprising effective amounts of pyruvate; an antioxidant, preferably Vitamin B acetate; and a mixture of saturated and unsaturated fatty acids.

The foregoing Martin patents do not disclose wound-healing compositions comprising pullulan, unlike the following patents.

U.S. Pat. No. 5,722,942 to Tanaka et al. discloses wound covering materials suitable for protection and treatment of wounds. The materials comprise: (a) 1 part by weight of glucomannan; (b) 0.20–0.99 part by weight of a solubility modifier comprising pullulan or carrageenan; (c) 0.10–12 parts by weight of a physiologically acceptable adhesive polymer base; and (d) 0.20–20 parts by weight of at least one plasticizer selected from the group consisting of polyhydric alcohols, sugar alcohols, monosaccharides, disaccharides and oligosaccharides. The materials are provided in the form of a film or a laminate of a film and another sheet material.

U.S. Pat. No. 5,618,799 to Inagi et al. discloses a powder preparation for healing damaged skin, which comprises: (a)50–90 wt. % sucrose; (b) 0.5–10 wt. % povidone-iodine; and (c) a water-soluble polymer selected from the group consisting of polyvinyl alcohol, polyvinyl pyrrolidone, polyacrylic acid and salts thereof, pullulan, carboxyvinyl polymers, methylcellulose, hydroxymethylcellulose, hydroxypropylmethylcellulose, and carboxymethylcellulose and salts thereof.

U.S. Pat. No. 4,844,898 to Komori et al. discloses a wound-healing preparation which comprises 50–90 wt. % of a sugar, 0.5–10 wt. % of povidone-iodine, 1–20 wt. % of water, 0.1–5 wt. % of an agent for imparting an appropriate consistency and stability selected from polysaccharides and derivatives thereof, and a buffer in an amount sufficient to adjust the pH of the preparation to 3.5–6. The polysaccharide can be, e.g., dextrin, gum arabic, pullulan, chondroitin sulfate, methylcellulose, sodium carboxymethylcellulose and the like.

U.S. Pat. No. 5,518,902 to Ozaki et al. discloses high pullulan content products, such as ointments and cosmetic packs. The products can include a variety of ingredients in addition to pullulan, such as other polysaccharides, polyhydric alcohols, and antiseptics.

U.S. Pat. No. 5,411,945 to Ozaki et al. discloses a pullulan binder and products produced therewith, including a facial pack. The products can include a variety of ingredients in addition to pullulan, such as other polysaccharides, antibacterial agents, pharmaceutically active substances and biologically active substances.

Despite the existence in the prior art of wound-healing compositions containing pullulan, there is still room for improvement in such compositions, and in processes for making them.

All references cited herein are incorporated herein by reference in their entireties.

SUMMARY OF THE INVENTION

The invention provides a bioadhesive composition comprising pullulan, pyruvate, an antioxidant, and a mixture of saturated and unsaturated fatty acids adapted to resuscitate injured mammalian cells. Also provided is a method for treating a wound, wherein a bioadhesive composition of the invention is applied to the wound.

DETAILED DESCRIPTION OF PREFERRED EMBODIMENTS

The bioadhesive composition of the invention comprises pullulan, pyruvate, an antioxidant, and a mixture of saturated and unsaturated fatty acids. Although the Martin patents teach the wound-healing effectiveness of a combination of pyruvate, antioxidant and a mixture of fatty acids, the inventors have discovered that pullulan acts as a surprisingly effective vehicle for topically administering the active ingredients.

Compositions of the invention preferably comprise pullulan in an amount of about 0.1 to about 80 wt. %, preferably about 40 to about 80 wt. % of the total weight of the composition.

A variety of pyruvate forms are suitable for use in the invention. The pyruvate is preferably selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, α-ketoglutaric acid, pharmaceutically acceptable salts of pyruvic acid, prodrugs of pyruvic acid, and mixtures thereof. More preferably, the pyruvate is sodium pyruvate. Pyruvate is preferably present in the composition in an amount of about 10 to about 50 wt. % of the total weight of the composition.

A suitable antioxidant is preferably selected from the group consisting of all forms of Vitamin A; all forms of carotene; all forms of Vitamin C; all forms of Vitamin E; Vitamin E esters which readily undergo hydrolysis to Vitamin E; prodrugs of Vitamin A, carotene, Vitamin C, and Vitamin E; pharmaceutically acceptable salts of Vitamin A, carotene, Vitamin C, and Vitamin E; and mixtures thereof. More preferably, the antioxidant is Vitamin E acetate. The antioxidant is preferably present in an amount of about 0.1 to about 40 wt. % of the total weight of the composition.

The mixture of saturated and unsaturated fatty acids preferably comprises animal and vegetable fats and waxes. More preferably, the fatty acid mixture includes fats selected from the group consisting of human fat, chicken fat, cow fat, sheep fat, horse fat, pig fat, and whale fat. The fatty acid mixture preferably comprises lauric acid, myristic acid, myristoleic acid, pentadecanoic acid, palmitic acid, palmitoleic acid, margaric acid, margaroleic acid, stearic acid, oleic acid, linoleic acid, linolenic acid, arachidic acid, and gadoleic acid. The mixture of saturated and unsaturated fatty acids is preferably present in an amount of about 10 to about 50 wt. % of the total weight of the composition.

The composition of the invention can further comprise water, pharmaceutically active agents, additional film-forming agents, plasticizing agents, additional flavoring agents, cooling agents, surfactants, stabilizing agents, emulsifying agents, thickening agents, binding agents, coloring agents, sweeteners, fragrances and the like. The composition is preferably in the form of a film, which can be employed as a physiologically acceptable vehicle for administering pharmaceutically active agents through the skin or open wounds of a patient as it adheres thereto.

The expression "physiologically acceptable" as used herein is intended to encompass compounds, which upon administration to a patient, are adequately tolerated without causing undue negative side-effects.

The expression "pharmaceutically active agents" as used herein is intended to encompass agents that promote a structural and/or functional change in and/or on bodies to which they have been administered. These agents are not particularly limited; however, they should be physiologically acceptable and compatible with the film. Suitable pharmaceutically active agents include, but are not limited to: immunostimulating agents (Betafectin™), antiviral agents, antikeratolytic agents, anti-inflammatory agents, antifungal agents, tretinoin, sunscreen agents, dermatological agents, topical antihistamine agents, antibacterial agents, other bioadhesive agents, respiratory bursting inhibitors (lactic acid, adenosine), inhibitors of prostaglandin synthesis (ibuprofen, aspirin, indomethacin, meclofenomic acid, retinoic acid, padimate O, meclomen, oxybenzone), steroidal anti-inflammatory agents (corticosteroids including synthetic analogs), antimicrobial agents (Neosporin® ointment, silvadine, triclosan), antiseptic agents, anesthetic agents (pramoxine hydrochloride, lidocaine, benzocaine), cell nutrient media, burn relief medications, sun burn medications, acne preparations, insect bite and sting medications, wound cleansers, wound dressings, scar reducing agents (vitamin E), and the like, and mixtures thereof, to further enhance the proliferation and resuscitation rate of mammalian cells.

Preferred antimicrobial agents include the essential oils (i.e., thymol, methyl salicylate, menthol and eucalyptol), copper gluconate, triclosan, polymyxin B sulfate, bacitracin zinc, and neomycin sulfate.

A particularly preferred wound-healing composition of the invention includes pullulan, pyruvate, an antioxidant, a mixture of saturated and unsaturated fatty acids, polymyxin B sulfate, bacitracin zinc, and neomycin sulfate. Preferably, the polymyxin B sulfate is present in an amount of about 1000 to about 15,000 units/gm, the bacitracin zinc is present in an amount of about 100 to about 1,500 units/gm, and the neomycin sulfate is present in an amount of about 1 to about 15 mg/gm.

The composition of the invention is preferably provided in the form of a film that adheres on contact to moist skin. Due to the relatively high oil content in the film, it is preferable to avoid substantial amounts of humectant in the film (and more preferable to have no humectant in the film), so as to avoid producing an overly moist, self-adhering film. In particular, it is preferred to formulate the film with a plasticizing agent other than glycerin, which is also a humectant. If the film includes a sweetener, it is preferable to use a sweetener other than sorbitol, which is a mild humectant.

Preferred plasticizing agents include triacetin in amounts ranging from about 0 to about 20 wt. %, preferably about 0 to about 2 wt. %. Other suitable plasticizing agents include monoacetin and diacetin.

Preferred cooling agents include physcool, in amounts ranging from about 0.001 to about 2.0 wt. %, preferably about 0.2 to about 0.4 wt. %. Other suitable cooling agents include WS3 and the like.

Preferred surfactants include Polysorbate 80 and Atlas 3000 (Atmos 300) in amounts ranging from about 0.5 to about 15 wt. %, preferably about 2 to about 5 wt. %. Other suitable surfactants include pluronic acid, sodium lauryl sulfate, and the like.

Preferred stabilizing agents include xanthan gum, locust bean gum and carrageenan, in amounts ranging from about 0 to about 10 wt. %, preferably about 0.01 to about 2 wt. %. Other suitable stabilizing agents include guar gum and the like.

Preferred emulsifying agents include triethanolamine stearate, quaternary ammonium compounds, acacia, gelatin, lecithin, bentonite, veegum, and the like, in amounts ranging from about 0 to about 5 wt. %, preferably about 0.01 to about 0.7 wt. %.

Preferred thickening agents include methylcellulose, carboxyl methylcellulose, and the like, in amounts ranging from about 0 to about 20 wt. %, preferably about 0.01 to about 5 wt. %.

Preferred binding agents include starch, in amounts ranging from about 0 to about 10 wt. %, preferably about 0.01 to about 2 wt. %.

Preferred film formers include pullulan, in amounts ranging from about 0.1 to about 80 wt. %, preferably about 30 to about 70 wt. %. Other suitable film formers include polyvinyl alcohol, suitable cellulose, and the like.

Suitable sweeteners that can be included are those well-known in the art, including both natural and artificial sweeteners. Suitable sweeteners include, e.g.

A. water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin;

B. water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like;

C. dipeptide based sweeteners, such as L-aspartic acid derived sweeteners, such as L-aspartyl-L-phenylalanine methyl ester (aspartame) and materials described in U. S. Pat. No. 3,492, 131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5, dihydrophenyl-glycine, L-aspartyl-2,5-dihydro-L-phenylalanine, L-aspartyl-L-(1-cyclohexyen)-alanine, and the like;

D. water-soluble sweeteners derived from naturally occurring water-soluble sweeteners, such as a chlorinated derivative of ordinary sugar (sucrose), known, for example, under the product description of sucralose; and E. protein based sweeteners such as thaumatoccous danielli (Thaumatin I and II).

In general, an effective amount of auxiliary sweetener is utilized to provide the level of sweetness desired for a particular composition, and this amount will vary with the sweetener selected. This amount will normally be 0.1% to about 10% by weight of the composition when using an easily extractable sweetener. The water-soluble sweeteners described in category A above, are usually used in amounts of about 0.1 to about 10 wt. %, and preferably in amounts of about 2 to about 5 wt. %. Some of the sweeteners in category A (e.g., glycyrrhizin) can be used in amounts set forth for categories B–E below due to the sweeteners' known sweetening ability. In contrast, the sweeteners described in categories B–E are generally used in amounts of about 0.1 to about 10 wt. %, with about 2 to about 8 wt. % being preferred and about 3 to about 6 wt. % being most preferred. These amounts may be used to achieve a desired level of sweetness independent from the flavor level achieved from any optional flavor oils used. Of course, sweeteners need not be added to films intended for non-oral administration.

The flavorings that can be used include those known to the skilled artisan, such as, natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, and citrus oil, including lemon, orange, grape, lime and grapefruit and fruit essences including apple, pear, peach, strawberry, raspberry, cherry, plum, pineapple, apricot and so forth. These flavorings can be used individually or in admixture. Commonly used flavors include mints such as peppermint, artificial vanilla, cinnamon derivatives, and various fruit flavors, whether employed individually or in admixture. Flavorings such as aldehydes and esters including cinnamyl acetate, cinnamaldehyde, citral, diethylacetal, dihydrocarvyl acetate, eugenyl formate, p-methylanisole, and so forth may also be used. Generally, any flavoring or food additive, such as those described in Chemicals Used in Food Processing, publication 1274 by the National Academy of Sciences, pages 63–258, may be used. Further examples of aldehyde flavorings include, but are not limited to acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl- 5-heptenal, i.e. melonal (melon); 2-6-dimethyloctanal (green fruit); and 2-dodecenal (citrus, mandarin); cherry; grape; mixtures thereof, and the like.

The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. In general, amounts of about 0.1 to about 30 wt. % are useable with amounts of about 10 to about 25 wt. % being preferred.

The compositions of this invention can also contain coloring agents or colorants. The coloring agents are used in amounts effective to produce the desired color. The coloring agents useful in the present invention, include pigments such as titanium dioxide, which may be incorporated in amounts of up to about 5 wt. %, and preferably less than about 1 wt. %. Colorants can also include natural food colors and dyes suitable for food, drug and cosmetic applications. These colorants are known as FD&C dyes and lakes. The materials acceptable for the foregoing spectrum of use are preferably water-soluble, and include FD&C Blue No. 2, which is the disodium salt of 5,5-indigotindisulfonic acid. Similarly, the dye known as Green No. 1 comprises a triphenylmethane dye and is the monosodium salt of 4-[4-N-ethyl-p-sulfobenzylamino)diphenyl-methylene]-[1-N-ethyl-N-p-sulfonium benzyl)-$\Delta^{2.5}$-cyclo-hexadienimine]. Additional examples include the yellow dye, known as D&C Yellow No. 10, and the dye known as FD&C Green No. 3, which comprises a triphenylmethane dye. A full recitation of all FD&C and D&C dyes and their corresponding chemical structures may be found in the Kirk-Othmer Encyclopedia of Chemical Technology, Volume 5, Pages 857–884, which text is accordingly incorporated herein by reference.

Methods for preparing films according to the invention are capable of encapsulating the oil ingredients within the film-forming matrix and maintaining the integrity of the film, even when the film contains oils in amounts of 10 wt. % or more.

In certain methods for preparing films according to the invention, the film-forming ingredients are mixed and hydrated with water separately from the water-soluble ingredients, which are mixed in aqueous solution separately from the organic ingredients (i.e., oils) and surfactants. In these methods, the final formulation is preferably produced by mixing the film-forming phase with the aqueous phase, then mixing in the organic phase, which includes surfactants, such as Polysorbate 80 and Atmos 300 (i.e., Atlas 3000).

The resulting formulation is cast on a suitable substrate and dried to form a film.

The film is preferably air-dried or dried under warm air and cut to a desired dimension, packaged and stored. The film preferably contains about 3% to about 8% moisture after drying.

The film-forming phase can include pullulan and stabilizing agents such as xanthan gum, locust bean gum and carrageenan. These ingredients are mixed and then hydrated in water for about 2 to about 48 hours to form a gel. The water is heated to a temperature of about 25 to about 45° C. to promote hydration. The amount of water is about 40 to 80 % of the gel. The resulting hydrated gel is then chilled to a temperature of about 20 to about 30° C. for about 2 to about 48 hours. The water is preferably deionized.

The aqueous phase can include ingredients such as coloring agent(s), copper gluconate and sweetener. The water is preferably deionized and the amount of water used is about 5 to about 80 wt. % of the final gel mixture.

If sodium saccharine and copper gluconate are both ingredients in the formulation, it is preferable to dissolve them separately in solution to avoid precipitation.

In a preferred method of producing films according to the invention, it is possible to hydrate the film-forming ingredients and combine all of the ingredients without heating. The preferred method of producing films comprises: (a) dissolving the water-soluble ingredients in water to form an aqueous mixture; (b) mixing the film-forming ingredients together in powder form to form a powder mixture; (c) adding the powder mixture to the aqueous mixture to form a hydrated polymer gel; (d) stirring the hydrated polymer at room temperature for about 1 to about 48 hours; (e) mixing the hydrophobic ingredients and surfactants to form an oil phase; (f) adding the oil phase to the hydrated polymer gel and mixing until uniform; (g) casting the uniform mixture on a suitable substrate; and (h) drying the cast mixture to form a film.

The preferred method can be conducted without hydrating the film-forming ingredients in hot water. Heating the ingredients increases energy costs in the manufacturing process. Moreover, heating results in undesirable losses of volatile ingredients to evaporation, which also affects the composition of the formulation. Further, mixing the oils in two steps minimizes the amount of flavor lost.

While not wishing to be bound by any theories, it is believed that the film-forming ingredients can be hydrated and mixed without heating due to an ionic effect known as the Donnan equilibrium. Hydrating the film-forming agents in the presence of electrolytes in solution effectively lowers the viscosity of the polymer gel being formed, thus increasing the efficiency of the hydrating process. The electrolytes are provided by the water-soluble ingredients of the formulation, which are dissolved in the hydration solution prior to addition of the film-forming ingredients.

It is preferable to avoid adding both copper gluconate and saccharin to the aqueous solution, as a precipitate will form. Thus, it is preferred to combine sweeteners other than saccharin with copper gluconate.

The invention will be illustrated in more detail with reference to the following Examples, but it should be understood that the present invention is not deemed to be limited thereto.

EXAMPLE 1

Antimicrobial/Wound-Healing Film

| NUMBER | INGREDIENT | WEIGHT (grams) |
|---|---|---|
| 1 | Xanthan Gum | 0.0385 |
| 2 | Locust Bean Gum | 0.0770 |
| 3 | Carrageenan | 0.3850 |

-continued

| NUMBER | INGREDIENT | WEIGHT (grams) |
|---|---|---|
| 4 | Pullulan | 18.5000 |
| 5 | Deionized Water | 84.2500 |
| 6 | Mineral Oil | 3.000 |
| 7 | Sodium Pyruvate | 0.2200 |
| 8 | Vitamin E | 0.2200 |
| 9 | Rendered Chicken Fat | 0.2200 |
| 10 | Polysorbate 80 | 0.4000 |
| 11 | Atlas 3000/Atmos 300 | 0.4000 |
| 12 | Triclosan | 0.0500 |

Ingredients 1–4 were dry mixed together and then added to ingredient 5 with further mixing to provide a gel phase. Ingredients 6–12 were mixed to uniformity in a separate container to provide an oil phase. The oil phase was then added to the gel phase with mixing and stored overnight.

The next day, the mixture was further mixed, poured on a mold and cast to form a film of a desired thickness at room temperature. The film was dried under warm air and cut to a desired dimension for testing.

The resulting film was slightly opaque and adhered to wet skin.

EXAMPLE 2

Antimicrobial/Wound-Healing Film

| NUMBER | INGREDIENT | WEIGHT (grams) |
|---|---|---|
| 1 | Xanthan Gum | 0.035 |
| 2 | Locust Bean Gum | 0.070 |
| 3 | Carrageenan | 0.350 |
| 4 | Pullulan | 18.000 |
| 5 | Deionized Water | 75.755 |
| 6 | Tween 80 | 0.400 |
| 7 | Atlas 3000/Atmos 300 | 0.400 |
| 8 | Polymyxin B Sulfate | 0.0035 |
| 9 | Bacitracin Zinc | 0.0319 |
| 10 | Neomycin Sulfate | 0.030 |
| 11 | Petrolatum, White | 4.135 |
| 12 | Vitamin E | 0.100 |
| 13 | Cocoa Butter | 0.120 |
| 14 | Olive Oil | 0.180 |
| 15 | Cottonseed Oil | 0.300 |
| 16 | Sodium Pyruvate | 0.100 |

Ingredients 1–4 were dry mixed together and then added to ingredient 5 with further mixing to provide a gel phase. Ingredients 8–16 were added to the gel phase in the form of 5.0 grams of Neosporin™ (Warner-Lambert Company, Morris Plains, N.J.) along with ingredients 6–7. The ingredients were mixed, poured on a mold and cast to form a film of a desired thickness at room temperature. The film was dried under warm air and cut to a desired dimension for testing.

The resulting film was not difficult to remove from the backing, but adhered to wet skin well. The film dried to a clear and shiny protective film on the skin.

EXAMPLE 3

Anesthetic Film

| NUMBER | INGREDIENT | WEIGHT (grams) |
|---|---|---|
| 1 | Xanthan Gum | 0.0385 |
| 2 | Locust Bean Gum | 0.077 |
| 3 | Carrageenan | 0.385 |
| 4 | Pullulan | 18.5 |
| 5 | Deionized Water | 54.25 |
| 6 | Deionized Water | 30 |
| 7 | BHT (hydroxybutyl toluene) | 0.03 |
| 8 | Mineral Oil | 3.0 |
| 9 | Lidocaine | 1.2 |
| 10 | Polysorbate 80 | 0.4 |
| 11 | Atlas 3000/Atmos 300 | 0.4 |

Ingredients 1–4 were dry mixed together and then added to ingredient 5 with further mixing to provide a gel phase. Ingredients 6–7 were mixed together in a separate container to provide an aqueous phase. Ingredients 8–11 were mixed to uniformity in a separate container to provide an oil phase. The aqueous phase was added to the gel phase, and then the oil phase was added to the gel/aqueous phase mixture with mixing.

The mixture was further mixed, poured on a mold and cast to form a film of a desired thickness at room temperature. The film was dried under warm air and cut to a desired dimension.

EXAMPLE 4

Antimicrobial/Wound-Healing Film

| NUMBER | INGREDIENT | WEIGHT (grams) |
|---|---|---|
| 1 | Xanthan Gum | 0.0385 |
| 2 | Locust Bean Gum | 0.077 |
| 3 | Carrageenan | 0.385 |
| 4 | Pullulan | 18.5 |
| 5 | Deionized Water | 54.25 |
| 6 | Copper Gluconate | 0.4 |
| 7 | Deionized Water | 30 |
| 8 | Mineral Oil | 3.0 |
| 9 | Sodium Pyruvate | 0.22 |
| 10 | Vitamin E | 0.22 |
| 11 | Rendered Chicken Fat | 0.22 |
| 12 | Polysorbate 80 | 0.4 |
| 13 | Atlas 3000/Atmos 300 | 0.4 |

Ingredients 1–4 were dry mixed together and then added to ingredient 5 with further mixing to provide a gel phase. Ingredients 6–7 were mixed together in a separate container to provide an aqueous phase. Ingredients 8–13 were mixed to uniformity in a separate container to provide an oil phase. The aqueous phase was added to the gel phase, and then the oil phase was added to the gel/aqueous phase mixture with mixing.

The mixture was further mixed, poured on a mold and cast to form a film of a desired thickness at room temperature. The film was dried under warm air and cut to a desired dimension.

While the invention has been described in detail and with reference to specific examples thereof, it will be apparent to one skilled in the art that various changes and modifications can be made therein without departing from the spirit and scope thereof.

What is claimed is:

1. A bioadhesive composition comprising a film forming phase, pyruvate, an antioxidant, and a mixture of saturated and unsaturated fatty acids adapted to resuscitate injured mammalian cells; said film forming phase comprising pullulan.

2. The composition according to claim 1, wherein said pyruvate is selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, α-ketoglutaric acid, pharmaceutically acceptable salts of pyruvic acid, prodrugs of pyruvic acid, and mixtures thereof.

3. The composition according to claim 2, wherein said pyruvate is sodium pyruvate.

4. The composition according to claim 1, wherein said antioxidant is selected from the group consisting of all forms of Vitamin A; all forms of carotene; all forms of Vitamin C; all forms of Vitamin E; Vitamin E esters which readily undergo hydrolysis to Vitamin E; prodrugs of Vitamin A, carotene, Vitamin C, and Vitamin E; pharmaceutically acceptable salts of Vitamin A, carotene, Vitamin C, and Vitamin E; and mixtures thereof.

5. The composition according to claim 4, wherein said antioxidant is Vitamin E acetate.

6. The composition according to claim 1, wherein said mixture of saturated and unsaturated fatty acids comprises animal and vegetable fats and waxes.

7. The composition according to claim 6, wherein said mixture of saturated and unsaturated fatty acids is selected from the group consisting of human fat, chicken fat, cow fat, sheep fat, horse fat, pig fat, and whale fat.

8. The composition according to claim 7, wherein said mixture of saturated and unsaturated fatty acids comprises lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gadoleic acid.

9. The composition according to claim 1, wherein said pullulan is present in an amount of about 0.1 to about 80 wt. %.

10. The composition according to claim 1, wherein said pyruvate is present in an amount of about 10 to about 50 wt. %.

11. The composition according to claim 1, wherein said antioxidant is present in an amount of about 0.1 to about 40 wt. %.

12. The composition according to claim 1, wherein said mixture of saturated and unsaturated fatty acids is present in an amount of about 10 to about 50 wt. %.

13. The composition of claim 1, further comprising polymyxin B sulfate, bacitracin zinc, and neomycin sulfate.

14. The composition of claim 13, wherein said polymyxin B sulfate is present in an amount of about 1000 to about 15,000 units/gm, the bacitracin zinc is present in an amount of about 100 to about 1,500 units/gm, and the neomycin sulfate is present in an amount of about 1 to about 15 mg/gm.

15. The composition of claim 14, wherein said pullulan is present in an amount of about 40 to about 80 wt. %, said pyruvate is present in an amount of about 10 to about 50 wt. %, said antioxidant is present in an amount of about 0.1 to about 40 wt. %, and said mixture of saturated and unsaturated fatty acids is present in an amount of about 10 to about 50 wt. %.

16. The composition of claim 1, further comprising an antimicrobially effective amount of at least one essential oil selected from the group consisting of thymol, methyl salicylate, eucalyptol and menthol.

17. The composition of claim 16, comprising about 40 to about 80 wt. % pullulan, about 10 to about 50 wt. % of said pyruvate, about 0.1 to about 40 wt. % of said antioxidant, about 10 to about 50 wt. % of said mixture of saturated and unsaturated fatty acids, about 0.1 to about 4 wt. % thymol, about 0.1 to about 4 wt. % methyl salicylate, about 0.1 to about 4 wt. % eucalyptol, about 0.1 to about 15 wt. % menthol, and about 0.1 to about 5 wt. % copper gluconate.

18. The composition of claim 1, further comprising about 0.01 to about 5 wt. % of at least one stabilizing agent, 0 to about 0.1 wt. % of at least one of at least one coloring agent, about 0.1 to about 8 wt. % of water, 0 to about 15 wt. % of at least one sweetening agent, 0 to about 15 wt. % of at least one flavoring agent, 0 to about 4 wt. % of at least one cooling agent, and about 0.1 to about 5 wt. % of at least one surfactant.

19. The composition of claim 18, wherein said least one stabilizing agent is selected from the group consisting of xanthan gum, locust bean gum and carrageenan, said at least one sweetening agent is selected from the group consisting of saccharin, aspartame and acesulfame K, said at least one cooling agent is physcool, and said at least one surfactant is selected from the group consisting of Polysorbate 80 and Atmos 300.

20. The composition of claim 1, in a form of a film that does not substantially adhere to itself.

21. The composition of claim 1, free of glycerin and sorbitol.

22. The composition of claim 1, free of humectants.

23. The composition of claim 1, wherein a total oil content of said composition is at least about 15 wt. %.

24. The composition of claim 1, wherein a total moisture content of said composition is about 3 wt. % to about 8 wt. %.

25. A method for treating a wound, said method comprising applying to said wound a composition according to claim 1.

* * * * *